United States Patent
Wada et al.

[11] Patent Number: 5,883,045
[45] Date of Patent: Mar. 16, 1999

[54] METHOD FOR THE TREATMENT OF PLANTS WITH AGROCHEMICAL TABLET COMPOSITIONS

[75] Inventors: Yuzuru Wada, Tokyo; Yuichi Otsu, Tochigi; Kunihiro Isono; Shigeharu Koyama, both of Tochigi; Shinzaburo Sone, Ibaraki, all of Japan

[73] Assignee: Nihon Bayer Agrochem K.K., Tokyo, Japan

[21] Appl. No.: 874,927

[22] Filed: Jun. 30, 1997

Related U.S. Application Data

[63] Continuation of Ser. No. 395,558, Feb. 28, 1995, abandoned.

[30]    Foreign Application Priority Data

Mar. 4, 1994    [JP]    Japan    .................................. 6-58345

[51] Int. Cl.⁶ .............................. A01N 25/08; A01N 25/34
[52] U.S. Cl. .......................... 504/116; 424/408; 424/464; 514/341; 514/772.3; 514/960
[58] Field of Search ............................ 504/116; 424/408, 424/464; 514/341, 772.3, 960

[56]    References Cited

U.S. PATENT DOCUMENTS

| | | | |
|---|---|---|---|
| 3,622,677 | 11/1971 | Short et al. | 71/77 |
| 3,673,181 | 6/1972 | Gutman | 71/86 |
| 4,017,505 | 4/1977 | Rogers et al. | 424/270 |
| 4,123,525 | 10/1978 | Ueno et al. | 71/DIG. 1 |
| 4,291,497 | 9/1981 | Manankov | 47/58 |
| 5,137,907 | 8/1992 | Kisida et al. | 514/406 |
| 5,162,052 | 11/1992 | Hoffmann et al. | 47/8 |
| 5,201,925 | 4/1993 | Itzel et al. | 47/58 |

FOREIGN PATENT DOCUMENTS 564 945    10/1993    European Pat. Off. .

OTHER PUBLICATIONS

Derwent Abstracts, abstract of JP 63–51,301 (1986).

*Primary Examiner*—S. Mark Clardy
*Attorney, Agent, or Firm*—Sprung Kramer Schaefer & Briscoe

[57]    ABSTRACT

Novel method for applying agrochemicals to plants, which method consists in attaching to the surface of the plants tablets comprising

- at least one agrochemically active compound and
- at least one adjuvant, which is solid, liquid of pasty at room temperature, and
- optionally, one or more excipients optionally in admixture with one or more other additives and/or water.

10 Claims, No Drawings

METHOD FOR THE TREATMENT OF PLANTS WITH AGROCHEMICAL TABLET COMPOSITIONS

This application is a continuation of application Ser. No. 08/395,558, filed Feb. 28, 1995, abandoned.

The present invention relates to a new method for applying agrochemicals to plants by means of tablets.

There are two application methods, which hitherto have been mostly employed for administering agrochemicals to plants.

The first method comprises applying the active ingredients by spraying liquid formulations or solid formulations in pulverized form onto the outer surface of the plants to be treated. The second method consists in mixing liquid or solid formulations of the active ingredients with the soil adjacent to the roots of the plants to be treated.

When working according to the spraying technique, the sprayed active ingredients reach the place of activity at a fast rate so that this method is featured by being a fast-acting one. However, a disadvantage of this method is that the major part of the sprayed active ingredients generally deposits on the soil and then drifts away from the treated zones leaving a rather low dosage of the active ingredients on the plants. Further, there is risk that the operators, who are spraying the formulations, become exposed to the chemicals during spraying the formulations.

Upon working according to the second of the two above-mentioned methods, i.e. mixing formulations with the soil, the risk of becoming contaminated with chemicals is markedly reduced for the operators, who are applying the formulations. However, this method suffers from the disadvantage that the desired effect can only be achieved, if active ingredients having systemic properties are used in the treatment. As compared with the application by means of spraying, the mixing technique is giving rise to the demerits that the biologicaal effect of the active ingredients emerges at a slower pace, the effective amounts of the active ingredients in the treatment become smaller due to absorption of the active ingredients in the soil and to drifting away by sprinkling with water, and a higher risk of a prolonged residual toxicity in the soil is inherent.

Considering the above-said, it is highly desirable to develop a novel control technique avoiding the above-mentioned disadvantages by using the active ingredients in an amount as small as possible and still maintaining a biological effect as high as possible.

Further, there has already been devised a method for the protection of trees, which method consists in boring a hole into the body of the tree and then injecting a liquid formulation of biologically active ingredients into the hole so that the formulation gradually penetrates into the interior of the tree like a transfusion of medicine for human beings. However, this method requires for the liquefaction of the active ingredients a great amount of solvents and/or surface active agents, which may be toxic to trees. In such treatment, the volumes of the liquid formulations applied for the protection of the trees inevitably become greater. Thus, the operators have to wait for a prolonged period of time until the penetration of the liquid formulations into the trees is complete. After the treatment, it is also necessary to recover the containers initially comprising the liquid formulations, which means that the working efficiency is poor. If great amounts of phytotoxic solvents and surface active agents are injected into the trees, the tissue of the tree bodies may collapse along the direction of longitudinal growing thereby hindering the circulation of water in the tissue, and further the injected liquids may cause an extensive collapse in plant body-forming layers that are located in the vicinity of the treated sites and are important for the growth of the trees. This may result in serious damages on the trees, such as extensive cleavages on the surface of the trees and so on. Consequently, it is highly desirable to develop a method of treatment, which can be carried out within a short period of time and which is not only entirely free from a risk for the operators of becoming exposed to the chemicals but also free from any phytotoxicity causing a growth inhibition of trees.

There has now been found a new method for applying agrochemicals to plants, which method consists in attaching to the surface of the plants tablets comprising at least one agrochemically active compound and at least one adjuvant, which is solid, liquid or pasty at room temperature, and optionally, one or more excipients optionally in admixture with one or more other additives and/or water.

It is also an object of the present invention to provide agrochemical formulations in tablet-form comprising at least one agrochemically active compound and at least one adjuvant, which is solid, liquid or pasty at room temperature, and optionally, one or more excipients optionally in admixture with one or more other additives and/or water.

It is decidedly surprising that the method according to the invention is outstandingly effective for applying agrochemicals to plants, since it could not be foreseen that the compositions in tablet-form are suitable for causing a sufficient penetration of the active ingredients into the plants.

When the tablet-form compositions are attached to the plants by the method according to the invention, the compositions ensure a sufficient application of the agrochemicals to the plants to achieve the desired effect, even if the active compounds are used in a far smaller amount than that to be used in the conventional spray application. Further, the method guarantees an effective control and does almost completely eliminate an undesired release of the agrochemicals to the environment. After all, there is no risk for the operators of becoming exposed to dusts or sprays of chemicals. Thus, the present invention provides an epoch-making method for plant treatment having a high-grade safety.

A particular advantage of the method according to the invention is that predetermined amounts of agrochemicals are metered and molded. Thus, the method is completely safe for the operators, since it liberates them from metering agrochemicals, which operation in many cases is liable for contaminating operators with chemicals. Further, the method is labor-saving in determining the desired dosage of active ingredients. Basically, by using the agrochemical formulations in tablet-form, sufficient control effects can be achieved to combat all animal pests or fungal diseases on the whole plant body without causing any phytotoxicity to the plant. It is only required to attach the tablets onto the stalk portions of the plant body nearest to the soil. Additionally, the tablets can also be applied onto non-lignified young trunks in the vicinity of new leaves, where heavy damages have been caused by fungal diseases or animal pests. It is also possible to attach the formulations in tablet-form onto the surface of the plant body after cuts have been formed thereon to the degree not to hinder the plant growth. After all, in the case of trees, the tablets can also be applied to portions from which the bark has been removed.

The compositions to be used for the treatment of plants according to the method of the invention contain one or more agrochemically active compounds, such as pesticidally active compounds, fungicidally active compounds, plant growth regulants and so on. Pesticidal compounds in the present context are compounds, which are suitable for the control of insects, acarides and/or nematodes infesting plants. Fungicidal compounds in the present context are compounds, which are suitable for combating fungal diseases infecting plants. Plant growth regulants in the present context are compounds, which interfere with the plant metabolism in a desired mode without damaging the plant. The compositions to be used according to the method of the invention may contain any of such agrochemical compounds, which have systemic properties.

The compositions in tablet-form to be used according to the method of the invention preferably contain one or more of the following compounds:

1-(6-chloro-3-pyridylmethyl)-N-nitro-imidazolidin-2-ylideneamine,
N-cyano-N-(2-chloro-5-pyridylmethyl)-N'-methyl acetoamidine,
1-[-(6-chloro-3-pyridylmethyl)-N-ethylamino]-1-methylamino-2-nitroethylene,
1-(2-chloro-5-pyridylmethyl)-3,5-dimethyl-2-nitroimino-hexahydro-1,3,5-triazine,
1-(2-chloro-5-thiazolylmethyl)-3,5-dimethyl-2-nitroimino-hexahydro-1,3,5-triazine,
0,0-dimethyl O-3-methyl-4-(methylsulfinyl)phenyl phosphorothioate,
trans-1,4,5,6-tetrahydro-1-methyl-2-[2-(3-methyl-2-thienyl)-vinyl]-pyrimidine tartrate,
(−)-(S)-2,3,5,6-tetrahydro-6-phenylimidazo[2,1-b] thiazole hydrochloride,
1-(4-chlorophenoxy)-3,3-dimethyl-1-(1,2,4-triazol-1-yl)-2-butanone,
all-rac-1-(biphenyl-4-yloxy)-3,3-dimethyl- 1-(1H-1,2,4-triazol-1-yl)-butan-2-ol,
2-p-chlorophenyl-2-(1H-1,2,4-triazol- 1-yl-methyl)-hexane nitrile,
(R,S)-2-(2,4-dichlorophenyl)-1-(1H-1,2,4-triazol-1-yl)-hexane-2-ol,
1-[2-(2,4-dichlorophenyl)-4-propyl- 1,3-dioxolan-2-yl methyl]-1H-1,2,4-triazole,
(E)-4-chloro-α,α,α-trifluoro-N-(1-imidazol-1-yl-2-propoxyethylidene)-O-toluidine,
N-propyl-N-[2-(2,4,6-trichlorophenoxy)-ethyl]-imidazol-1-yl carboxamide,
pent-4-enyl N-furfuryl-N-imidazol-1-yl carbonyl-DL-homoalaninate,
2,4'-dichloro-α-(pyrimidin-5-yl)-benzhydryl alcohol,
(E)-(R,S)-1-(4-chlorophenyl)-4,4-dimethyl-2-(1H-1,2,4-triazol-1-yl)-1-pentene-3-ol,
(E)-(S)-1-(4-chlorophenyl)-4,4-dimethyl-2-(1H-1,2,4-triazol-1-yl)-penta-1-ene-3-ol,
(R,S)-1-(4-chlorophenyl)-4,4-dimethyl-3-(1H-1,2,4-triazol-1-ylmethyl)-pentan-3-ol,
2',4'-dichloro-2-(3-pyridyl)-acetophenone (E,Z)-0-methyloxime,
1,4-bis-(2,2,2-trichloro-1-formamidoethyl)-piperazine,
(2RS,3RS)-1-(4-chlorophenyl)-4,4-dimethyl--2-(1H-1,2,4-triazol-1-yl)pentan-3-ol,
(±)-cis-4-[3-(4-tert-butylphenyl-2-methylpropyl]-2,6-dimethylmorpholine, and
2-(4-fluorophenyl)-2-(1,2,4-triazol-2-ylmethyl)-3-(2-chlorophenyl)-epoxyethane.

The compositions in tablet-form to be used according to the method of the invention do contain at least one adjuvant, which is solid, liquid or pasty at room temperature. Such adjuvants preferably are selected from fatty acid polyhydric alcohol esters, polyalkylene oxide addition products of fatty acid polyhydric alcohol esters, polyalkylene oxide fatty acid esters, polyalkylene oxide lanolins, sorbitol lanolin derivatives, polyalkylene oxide bees wax, sorbitol bees wax derivatives, polysaccharides, polysaccharide derivatives, higher alcohols having at least eight carbon atoms, polyalkylene oxides, graft polymers of polyalkylene oxides, block polymers of polyalkylene oxides, and random polymers of polyalkylene oxides.

As examples of such adjuvants, there may be mentioned fatty acid polyhydric alcohol esters, such as sorbitan monolaurate, sorbitan monooleate, and sorbitan trioleate, etc., polyalkylene oxide addition products of fatty acid polyalcohol esters, such as polyoxyethylene sorbitan monolaurate, polyoxyethylene sorbitan monooleate, polyoxyethylene sorbitan tristearate, etc., polyalkylene oxide fatty acid esters, such as polyoxyethylene laurate, polyoxyethylene oleate, and polyoxyethylene stearate, etc., polysaccharides, such as starch, cellulose, sucrose, natural rubber, carboxymethyl cellulose, methyl cellulose, hydroxypropylene cellulose and sucrose stearate, etc., higher alcohols, such as lauryl alcohol, etc., polylalkylene oxides, their graft polymers, block polymers, and random polymers, such as polyethylene glycol, polypropylene glycol, polyglycerin, polyoxyethylene oxypropylene block polymer and polyoxyethylene polyoxypropylene block polymer glycerine ether, etc..

As preferred examples of the adjuvants to be employed in the method of the present invention, there may be mentioned sorbitan monostearate, polyoxyethylene sorbitan tristearate, polyethylene glycol (#4000), polyethylene glycol (#6000), oleic acid polyethylene glycol ester, polyoxyethylene lanolin, polyoxyethylene polyoxypropylene block polymer, polyoxyethylene bees wax, hydroxypropyl cellulose, crystalline cellulose, sucrose stearate and carboxymethyl cellulose.

The compositions in tablet-form to be used according to the invention may comprise one or more excipients optionally in admixture with one or more additives and/or water.

As examples of excipients, there may be mentioned lignin, lignin derivatives and mineral materials represented by clay, talc, amorphous silicon dioxide.

Additives in the present context are customary components, which can be used in compositions of the instant type without deteriorating the biological properties of said compositions. Examples of such additives are stabilizers, lubricants, colorants and binders.

Preferred stabilizers are anti-oxidants and chemicals capable of protecting the molded formulations from undesirable degradation that may take place during processing operations such as ultra-violet ray irradiation and extrusion. A stabilizer, such as epoxidized soya-bean oil, for instance, can be employed as secondary plasticizer. Preferred lubricants to be employed include stearates, stearic acid and low-molecular polyethylene. These compounds can be used in a concentration up to 20% by weight in the compositions.

The concentration of the agrochemicals in the tablet-form compositions to be used according to the invention can be varied within a relatively wide range. In general, the compositions contain from about 1 to about 50 parts by weight, preferably from about 1 to about 20 parts by weight of one or more active ingredients per 100 parts by weight of the formulation.

The concentration of adjuvants in the tablet-form compositions to be used in the method according to the invention can also be varied within a relatively wide range. In general, the compositions contain from about 50 to 99 parts by weight, preferably from about 80 to about 99 parts by weight of one or more adjuvants, optionally in admixture with one or more excipients, other additives and/or water, per 100 parts by weight of the formulation.

The amounts of the active ingredients to be employed in the method according to the invention can also be varied within a certain range depending on the kind and degree of activity of the active ingredients.

The compositions in tablet-form to be employed in the method according to the invention can be prepared by conventional known methods for the production of tablets, such as by the extrusion method, the injection molding method, the compression molding method (tableting method), the melt molding method, and the like.

Upon treating plants according to the method according to the invention, the compositions in tablet-form are attached onto surfaces of stalks or trunks of plant bodies, thereby to let the active ingredients penetrate into the plant bodies, exhibiting the desired action and effects and thus achieving plant treatment.

The method according to the invention can generally be employed to control all kinds of animal pests infesting plants. As examples of insects, there are mentioned:

From the order of Coleoptera, e.g. *Callosobruchus chinensis, Sitophilus zeamais, Tribolium castaneum, Epilachna vigintioctomaculata, Agriotes fuscicollis, Anomala rufocuprea, Leptinotarsa decemlineata,* Diabrotica spp., *Monochamus alternatus, Lissorhoptrus oryzophilus, Lyctus bruneus;* from the order of Lepidoptera, e.g., *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella maculipennis, Heliothis virescens, Phyllocnistis citrella;* from the order of Hemiptera, e.g. *Nephotettix cincticeps, Nilaparvata lugens, Pseudococcus comstocki, Unaspis yanonensis, Myzus persicae, Aphis pomi, Aphis gossypii, Rhopalosiphum pseudobrassicas, Stephanitis nashi,* Nezara spp., *Cimex lectularius, Trialeurodes vaporariorum,* Psylla spp.; from the order to Orthoptera, e.g. *Blatella germanica, Periplaneta americana, Gryllotalpa africana, Locusta migratoria migratoriodes;* from the order of Isoptera, e.g. *Reticulitermes speratus, Coptotermes formosanus;* from the order of Azaminura, e.g. *Thrips palmi Karny;* from the order of Diptera, e.g. *Musca domestica, Aedes aegypti, Hylemia platura; Celux pipiens, Anopheles sinensis, Culex tritaeniorhynchus.*

As examples of mites, there may be mentioned *Tetranychus telarius, Tetranychus urticae, Panonychus citri, Aculops pelekassi,* Tarsonemus spp., and the like.

As examples of nematodes, there may be mentioned *Meliodogyne incognita, Bursaphelenchus lignicolus* Mamiya et Kiyohara, *Aphelenchoides besseyi, Heterodera glycines,* Pratylenchus spp., and the like.

The method according to the invention can also be generally employed to control all kinds of fungal diseases infecting plants. As examples of such fungal diseases, there may be mentioned various plant blights caused by Plasmodiophoromycetes, Oomycetes, Chytridiomycetes, Zygomycetes, Ascomycetes, Basidiomycetes, Deuteromycetes, and those caused by Pseudomonodaceae, Rhizobiaceae, Enterobacteriaceae, Corynebacteriaceae and Streptomyceteceae.

The method according to the invention can also be used to apply all kinds of growth regulators, such as compounds improving the growth of plants, accellerating the growth, inhibiting the internodal growth and so on.

The method according to the invention can be employed for the treatment of various plants, to which tablets can be attached. Preferably, the method can be used for the treatment of fruit vegetables, flowers and ornamental plants and trees such as, for example, tomatoes, eggplants, cucumbers, roses, chrysanthemum, pine trees (black pines, red pines, larches, common spruce), Japanese cedars, Japanese cypresses and so on, further Hiba cypresses, chestnut trees, apple trees, pears, peaches, plums, cherry trees, persimmons and so on.

The preparation of the compositions in tablet-form and their use according to the method of the invention are illustrative by the following examples. The technical scope of the invention, however, is not limited by the examples to any extent.

EXAMPLES

Examples of active components

Imidacloprid: 1-(6-chloro-3-pyridylmethyl)-N-nitroimidazolidine-2-ylideneamine,

Triadimefon: 1-(4-chlorophenoxy)-3,3-dimethyl-1-(1,2,4-triazol-1-yl)-2-butanone, Compound A: N-cyano-N-(2-chloro-5-pyridylmethyl)-N'-methylacetoamidine, Compound B: 1-[N-(6-chloro-3-pyridylmethyl)-N-ethyl amino]-1-methylamino-2-nitroethylene.

The compositions to be used in the method according to the invention were prepared by intimately mixing the components mentioned in the following examples in the stated amounts and forming tablets by means of a tabletting press or by melt molding. The tablets, in each case, had a diameter of 6 mm and a weight of 40 mg.

|  | (parts by weight) |
|---|---|
| Example 1 | |
| Imidacloprid | 15 |
| Sorbitan monolaurate | 74 |
| Amorphous silicon dioxide | 10 |
| Calcium stearate | 1 |
| Example 2 | |
| Imidacloprid | 15 |
| Polyoxyethylene sorbitan tristearate | 74 |
| Amorphous silicon dioxide | 10 |
| Calcium stearate | 1 |
| Example 3 | |
| Triadimefon | 1.5 |
| Polyethylene glycol (#4000) | 97.5 |
| Calcium stearate | 1.0 |
| Example 4 | |
| Triadimefon | 1.5 |
| Oleic acid-polyethylene glycol ester | 45.5 |
| Amorphous silicon dioxide | 15.5 |
| crystalline cellulose | 37.0 |
| Calcium stearate | 1.0 |
| Example 5 | |
| Imidacloprid | 15.0 |
| Triadimefon | 1.5 |
| Polyoxyethylene lanolin | 40.5 |
| Amorphous silicon dioxide | 15.0 |

-continued

| | (parts by weight) |
|---|---|
| Polyoxyethylene polyoxypropylene block polymer | 27.0 |
| Calcium stearate | 1.0 |

Example 6

| | |
|---|---|
| Imidacloprid | 15.0 |
| Triadimefon | 1.5 |
| Polyoxyethylene bees wax | 40.5 |
| Amorphous silicon dioxide | 15.0 |
| Hydroxypropyl cellulose | 27.0 |
| Calcium stearate | 1.0 |

Example 7

| | |
|---|---|
| Imidacloprid | 15.0 |
| Triadimefon | 1.5 |
| Sucrose stearate | 82.5 |
| Calcium stearate | 1.0 |

Example 8

| | |
|---|---|
| Imidacloprid | 15 |
| Polyethylene glycol (#6000) | 84 |
| Calcium stearate | 1 |

Example 9

| | |
|---|---|
| Imidacloprid | 7.5 |
| Polyethylene glycol (#6000) | 91.5 |
| Calcium stearate | 1.0 |

Example 10

| | |
|---|---|
| Imidacloprid | 15 |
| Carboxymethyl cellulose | 84 |
| Calcium stearate | 1 |

Example 11

| | |
|---|---|
| Imidacloprid | 7.5 |
| Carboxymethyl cellulose | 91.5 |
| Calcium stearate | 1.0 |

Example 12

| | |
|---|---|
| Compound A | 15 |
| Polyethylene glycol (#6000) | 84 |
| Calcium stearate | 1 |

Example 13

| | |
|---|---|
| Compound A | 7.5 |
| Polyethylene glycol (#6000) | 91.5 |
| Calcium stearate | 1.0 |

Example 14

| | |
|---|---|
| Compound A | 15 |
| Carboxymethyl cellulose | 84 |
| Calcium stearate | 1 |

Example 15

| | |
|---|---|
| Compound A | 7.5 |
| Carboxymethyl cellulose | 91.5 |
| Calcium stearate | 1.0 |

Example 16

| | |
|---|---|
| Compound B | 15 |
| Polyethylene glycol (#6000) | 84 |
| Calcium stearate | 1 |

Example 17

| | |
|---|---|
| Compound B | 7.5 |
| Polyethylene glycol (#6000) | 91.5 |
| Calcium stearate | 1.0 |

Example 18

| | |
|---|---|
| Compound B | 15 |
| Carboxymethyl cellulose | 84 |
| Calcium stearate | 1 |

Example 19

| | |
|---|---|
| Compound B | 7.5 |
| Carboxymethyl cellulose | 91.5 |
| Calcium stearate | 1.0 |

USE EXAMPLES

Example A

Efficacy tests on vegetables against aphids Tested crops: Cucumber (var. Suyo) and eggplant (var. Senryo ni gou) The vegetables at the growth stage of 8 leaves were used in this test.

Pest species: *Aphis gossypii* (wild strain) for cucumber and *Myzus persicae* (organophosphorus and carbamate insecticides resistant strain) for eggplant were used in this test.

Plot size and replications: Two plants in one pot (15 cm in diameter) per plot and two replications.

Date of application: In the beginning of October

Application method

About 200 heads of *Aphis gossypii* or 120 heads of *Myzus persicae* were attached artificially on each test plant one day before the application. Disk shape tablets (6 mm in diameter, 1 mm in thickness) described above (Examples 1, 2, 8, 12 and 16) and the tablets of Comparative Examples 1,2 and 3 were formulated. The tablet formulations were applied on the test plants at a height of 8 cm above the soil surface.

| | (parts by weight) |
|---|---|
| Comparative Example 1: | |
| Imidacloprid | 15 |
| Polyoxyethylene laurylether | 74 |
| Amorphous silicon dioxide | 10 |
| Calcium stearate | 1 |
| Comparative Example 2: | |
| Imidacloprid | 15 |
| Polyoxyethylene nonylphenylether | 74 |
| Amorphous silicon dioxide | 10 |
| Calcium stearate | 1 |
| Comparative Example 3: | |
| Imidacloprid | 15 |
| Vaseline | 74 |
| Amorphous silicon dioxide | 10 |
| Calcium stearate | 1 |

On the test day, *Aphis gossypii* was inoculated at a rate of 70 heads per stand in the cucumber test district, and in the eggplant test district, *Myzus persicae* was inoculated at a rate of 50 heads per stand.

Evaluation method: Before the application and 7 days, 14 days, 21 days after the application, the numbers of aphids infesting the test plants were counted. After every evaluation about 100 heads of aphids were further attached to the test plants. Phytotoxicity was also evaluated and rated from 0 to 5 at the day of evaluation.

Scale for the evaluation of the phytotoxicity:

0: No phototoxicity

1: Slight necrosis of leaf margin or slight leaf spotting

2: necrosis on leaf margin or leaf spotting

3: necrosis of leaf margin even on emerged leaves

4: phytotoxicity apparent with growth inhibition

5: completely withered

The test results are shown in Tables 1 and 2.

TABLE 1

Test vegetable: Cucumber
Test pest: *Aphis gossypii*

| Formulation | Active ingredient mg/plant | Control effect (%) | | | Phytotoxicity |
|---|---|---|---|---|---|
| | | 7th day | 14th day | 21st day | |
| Example 1 | 6 | 100 | 95 | 95 | 0 |
| Example 2 | 6 | 100 | 98 | 97 | 0 |
| Example 8 | 6 | 100 | 99.9 | 99 | 0 |
| Example 12 | 6 | 100 | 99 | 98 | 0 |
| Example 16 | 6 | 100 | 99 | 97 | 0 |
| Comparative Example 1 | 6 | 100 | — | — | 5 |
| Comparative Example 2 | 6 | 100 | 98 | 96 | 4 |
| Comparative Example 3 | 6 | 60 | 58 | 42 | 0 |
| Untreated | — | 0 | 0 | 0 | 0 |
| Number of aphids/plant (77 heads before the treatment) | | 421 | 491 | 334 | |

TABLE 2

Test vegetable: Eggplant
Test pest: *Myzus persicae*

| Formulation | Active ingredient mg/plant | Control effect (%) | | | Phytotoxicity |
|---|---|---|---|---|---|
| | | 7th day | 14th day | 21st day | |
| Example 1 | 6 | 90 | 98 | 95 | 0 |
| Example 2 | 6 | 91 | 98 | 97 | 0 |
| Example 8 | 6 | 98 | 99 | 99 | 0 |
| Example 12 | 6 | 78 | 95 | 87 | 0 |
| Example 16 | 6 | 80 | 95 | 90 | 0 |
| Comparative Example 1 | 6 | 95 | 100 | — | 5 |
| Comparative Example 2 | 6 | 92 | 98 | 90 | 4 |
| Comparative Example 3 | 6 | 42 | 38 | 25 | 0 |
| Untreated | — | 0 | 0 | 0 | 0 |
| Number of aphids/plant (57 heads before the treatment) | | 258 | 1201 | 514 | |

What is claimed is:

1. A method for applying agrochemicals to plants, which method consists in attaching tablets comprising
   at least one agrochemically active compound and
   at least one adjuvant, which is solid, liquid or pasty at room temperature, and
   optionally, one or more excipients optionally in admixture with one or more other additives and/or water,
   to the surface of the plants.

2. A method according to claim 1, wherein the tablets comprise at least one agrochemically active compound selected from
   1-(6-chloro-3-pyridylmethyl)-N-nitro-imidazolidin-2-ylideneamine,
   N-cyano-N-(2-chloro-5-pyridylmethyl)-N'-methyl acetoamidine,
   1-[N-(6-chloro-3-pyridylmethyl)-N-ethylamino]-1-methylamino-2-nitroethylene,
   1-(2-chloro-5-pyridylmethyl)-3,5-dimethyl-2-nitroimino-hexahydro-1,3,5-triazine,
   1-(2-chloro-5-thiazolylmethyl)-3,5-dimethyl-2-nitroimino-hexahydro-1,3,5-triazine,
   0,0-dimethyl O-3-methyl-4-(methylsulfinyl)-phenyl phosphorothioate,
   trans-1,4,5,6-tetrahydro-1-methyl-2-[2-(3-methyl-2-thienyl)-vinyl]-pyrimidine tartrate,
   (−)-(S)-2,3,5,6-tetrahydro-6-phenylimidazo[2,1-b] thiazole hydrochloride,
   1-(4-chlorophenoxy)-3,3-dimethyl-1-(1,2,4-triazol-1-yl)-2-butanone,
   all-rac-1-(biphenyl-4-yloxy)-3,3-dimethyl-1-(1H-1,2,4-triazol-1-yl)-butan-2-ol,
   2-p-chlorophenyl-2-(1H-1,2,4-triazol-1-yl-methyl)-hexane nitrile,
   (R,S)-2-(2,4-dichlorophenyl)-1-(1H-1,2,4-triazol-1-yl)-hexan-2-ol,
   1-[2-(2,4-dichlorophenyl)-4-propyl-1,3-dioxolan-2-yl-methyl]-1H-1,2,4-triazole,
   (E)-4-chloro-α,α,α-trifluoro-N-(1-imidazol-1-yl-2-propoxyethylidene)-O-toluidine,
   N-propyl-N-[2-(2,4,6-trichlorophenoxy)-ethyl]-imidazol-1-yl carboxamide,
   pent-4-enyl N-furfuryl-N-imidazol-1-yl carbonyl-DL-homoalaninate,
   2,4'-dichloro-α-(pyrimidin-5-yl)-benzhydryl alcohol,
   (E)-(R,S)-1-(4-chlorophenyl)-4,4-dimethyl-2-(1H-1,2,4-triazol-1-yl)-1-pentene-3-ol
   (E)-(S)-1-(4-chlorophenyl)-4,4-dimethyl-2-(1H-1,2,4-triazol-1-yl)-pent-1-ene-3-ol,
   (R,S)-1-(4-chlorophenyl)-4,4-dimethyl-3-(1H-1,2,4-triazol-1-ylmethyl)-pentan-3-ol,
   2',4'-dichloro-2-(3-pyridyl)-acetophenone (E,Z)-0-methyloxime,
   1,4-bis-(2,2,2-trichloro- 1-formarnidoethyl)-piperazine,
   (2RS,3RS)-1-(4-chlorophenyl)-4,4-dimethyl--2-(1H-1,2,4-triazol-1-yl)-pentan-3-ol,
   (±)-cis-4-[3-(4-tert-butylphenyl)-2-methylpropyl]-2,6-dimethylmorpholine, and
   2-(4-fluorophenyl)-2-( 1,2,4-triazol-2-ylmethyl)-3-(2-chlorophenyl)-epoxyethane.

3. A method according to claim 1, wherein the tablets comprise at least one adjuvant, selected from fatty acid polyhydric alcohol esters, polyalkylene oxide addition products of fatty acid polyhydric alcohol esters, polyalkylene oxide fatty acid esters, polyalkylene oxide lanolins, sorbitol lanolin derivatives, polyalkylene oxide bees wax, sorbitol bees wax derivatives, polysaccharides, polysaccharide derivatives, higher alcohols having at least eight carbon atoms, polyalkylene oxides, graft polymers of polyalkylene oxides, block polymers of polyalkylene oxides, and random polymers of poklyalkylene oxides.

4. A method according to claim 1, wherein the tablets comprise at least one adjuvant selected from sorbitan monostearate, polyoxyethylene sorbitan tristearate, polyethylene glycol (#4000), polyethylene glycol (#6000), oleic acid polyethylene glycol ester, polyoxyethylene lanolin, polyoxyethylene polyoxypropylene block polymer, polyoxyethylene bees wax, hydroxypropyl cellulose, crystalline cellulose, sucrose stearate, and carboxymethyl cellulose.

5. A method according to claim 1, wherein the agrochemically active compound is at least one fungicidally active compound and/or at least one pesticidally active compound.

6. A method according to claim 1, wherein the agrochemically active compound is at least one plant growth regulant.

7. The method according to claim 1, wherein the compound is 1-(6-chloro-3-pyridylmethyl)-N-nitro-imadazolidine-2-ylideneamine.

8. A composition in tablet-form comprising, per 100 parts by weight of the composition, the following:
(A) about 1 to about 20 parts by weight of at least one agrochemically active compound;
(B) about 80 to about 99 parts by weight of at least one adjuvant, which is solid, liquid or pasty at room temperature and is selected from the group consisting of fatty acid polyhydric alcohol esters, polyalkylene oxide addition products of fatty acid polyhydric alcohol esters, polyalkylene oxide fatty acid esters, polyalkylene oxide lanolins, sorbitol lanolin derivatives, polyalkylene oxide bees wax, sorbitol bees wax derivatives, polysaccharides, polysaccharide derivatives, higher alcohols having at least eight carbon atoms, polyalkylene oxides, graft polymers of polyalkylene oxides, block polymers of polyalkene oxides, and random polymers of polyalkylene oxides
(C) optionally, one or more excipients optionally in admixture with one or more other additives and/or water.

9. The composition according to claim 8, wherein the agrochemically active compound is 1-(6-chloro-3-pyridylmethyl)-N-nitro-imadazolidine-2-ylideneamine.

10. The composition according to claim 8, wherein the tablets comprise at least one adjuvant selected from the group consisting of sorbitan monostearate, polyoxyethylene sorbitan tristearate, polyethylene glycol (#4000), polyethylene glycol (#6000), oleic acid polyethylene glycol ester, polyoxyethylene lanolin, polyoxyethylene polyoxypropylene block polymer, polyoxyethylene bees wax, hydroxypropyl cellulose, crystalline cellulose, sucrose stearate, and carboxymethyl cellulose.

* * * * *

UNITED STATES PATENT AND TRADEMARK OFFICE
CERTIFICATE OF CORRECTION

PATENT NO. : 5,883,045
DATED : March 16, 1999
INVENTOR(S) : Yuzuru Wada, et al

It is certified that error appears in the above-identified patent and that said Letters Patent is hereby corrected as shown below:

Col. 10, Line 35    Delete "formarnidoethyl" and substitute –formamidoethyl--

This certificate supersedes Certificate of Correction issued November 16, 1999.

Signed and Sealed this

Fourth Day of April, 2000

Attest:

Q. TODD DICKINSON

Attesting Officer

Director of Patents and Trademarks